United States Patent [19]

Blair

[11] 4,430,329
[45] Feb. 7, 1984

[54] SYNERGISTIC TREATMENT OF ADULT CANINE HEARTWORM WITH THIACETARSAMIDE AND IVERMECTIN

[75] Inventor: Lyndia S. Blair, Annandale, N.J.
[73] Assignee: Merck & Co., Inc., Rahway, N.J.
[21] Appl. No.: 379,233
[22] Filed: May 17, 1982
[51] Int. Cl.$^3$ .................... A61K 31/71; A61K 31/285
[52] U.S. Cl. .................................. 424/181; 424/180; 424/297
[58] Field of Search ....................... 424/180, 181, 297

[56] References Cited

U.S. PATENT DOCUMENTS 4,199,569  4/1980  Chabala et al. .
4,310,519  1/1982  Albers-Schonberg et al. .

OTHER PUBLICATIONS

Journal of American Veterinary Medical Assoc. 142 pp. 23–26., (1963) Jackson.
Proceedings of Heartworm Symposium–1980, Jackson et al., (I) p. 137–140, Otto, Editor, Veterinary Medicine Publishing Co. (1981).
Proceedings of Heartworm Symposium–1980, Jackson et al., (II), pp. 153–156, Otto, Editor, Veterinary Medicine Publishing Co. (1981).
American Journal of Veterinary Research 40, Blair et al., pp. 1031–1032 (1979).
Journal of Helminthology 52, Campbell et al., pp. 308—310, (1978).
Proceedings of Heartworm Symposium–1980, pp. 182–184, Otto, Editor, Veterinary Medicine Publishing Co. (1981).

*Primary Examiner*—Sam Rosen
*Attorney, Agent, or Firm*—David L. Rose; Mario A. Monaco

[57] ABSTRACT

There is disclosed a method for the treatment of adult canine heartworm which involves treating a dog infected with adult heartworm first with thiacetarsamide and then, following a period of from 3 to 6 weeks, with ivermectin. The thiacetarsamide which has some activity against the adult heartworm has this activity potentiated or synergized by the ivermectin.

4 Claims, No Drawings

SYNERGISTIC TREATMENT OF ADULT CANINE HEARTWORM WITH THIACETARSAMIDE AND IVERMECTIN

BACKGROUND OF THE INVENTION

Adult canine heartworm (*Dirofilaria immitis*) reside in the right ventrical and the adjacent blood-vessels of the host dog. The female heartworm deposits microfilaria which enter the bloodstream. These microfilaria cannot further develop unless they are ingested by the intermediate host, which consists of various mosquito species. Within the mosquito, the microfilaria develope into the third stage (infective larvae). The larvae gain entrance to the dog upon refeeding by the mosquito and after a period of several months migrate to the heart where they mature into adults.

The condition is most prevalent in coastal areas but can occur anywhere with an indigenous mosquito population and infected dogs. Treatment of both the adult and microfilaria has proven to be very difficult.

Thiacetarsamide is a known agent for the treatment of adult canine heartworm (see Jackson *Journal of the American Veterinary Medical Association* 142, pages 23-26 (1963) and Jackson et al. *Proceedings of the Heartworm Symposium*—1980, pages 137-140, Otto, Editor, Veterinary Medicine Publishing Company (1981)). However the drug is not entirely efficacious and the percentage of adult worms killed following the normally prescribed two or three day regimen treatment may only range from 60 to 70 percent (see Jackson et al. *Proceedings of the Heartworm Symposium*—1980, pages 153-156, Otto, Editor, Veterinary Medicine Publishing Company (1981)).

Ivermectin and other related avermectin compounds are a new group of antiparasitic compounds of microbial origin and are described in U.S. Pat. Nos. 4,310,519 to Albers-Schonberg et al. and 4,199,569 to Chabala et al. Within the broad range of activities possessed by these compounds, they have been found to be very active against the microfilarial stage of canine heartworm. (See Blair et al. *American Journal of Veterinary Research*, 40, pages 1031-1032 (1979) and Campbell et al. *Journal of Helminthology*, 52, pages 308-310 (1978)). However, the avermectins have been found to be substantially ineffective against adult canine heartworm when used alone. (See Jackson et al. Supra, page 136).

It has been surprisingly found that the administration of ivermectin at 3 to 6 weeks after the administration of thiacetarsamide dramatically increases the activity of the combination against the adult worms.

SUMMARY OF THE INVENTION

The instant invention is concerned with the treatment of adult canine heartworms. More specifically it is concerned with the use of thiacetarsamide, an agent known as being somewhat active against adult heartworm, and following 3 to 6 weeks after such thiacetarsamide treatment the administration of ivermectin. Thus, it is an object of this invention to describe the treatment of adult canine heartworm using the above-described treatment regimen. A further object of this invention is to describe the formulations and doses used for such treatments. Further objects will become apparent from a reading of the following description.

DESCRIPTION OF THE INVENTION

The treatment of adult canine heartworm has been very difficult to achieve. At this time, only one drug is approved by the Counsel of the American Veterinary Medical Association and the Executive Committee of the American Heartworm Society. That drug is thiacetarsamide, however, as noted Supra in Jackson et al. the treatment is not always efficacious. It has been found that the efficacy of thiacetarsamide can be dramatically improved by administering ivermectin or a related avermectin compound at from 3 to 6 weeks after the thiacetarsamide treatment. Ivermectin itself has no demonstrable activity against adult canine heartworm thus the dramatic improvement in efficacy is highly surprising.

In the normal course of treatment thiacetarsamide is administered intravenously to dogs at a rate of 1 mg per pound (2.2 mg/kg). This treatment is given twice a day for 2 or 3 consecutive days. (See Jackson et al. Supra page 153 and "Recommended Procedures for the Management of Canine Heartworm Disease" in *Proceedings of the Heartworm Symposium*—1980 pages 182-184, Otto Editor, Veterinary Medicine Publishing Company (1981)).

Starting at from 3 to 6 weeks after the thiacetarsamide treatment the ivermectin is administered. A single oral or parenteral dose of about 0.05 to 0.3 mg/kg preferably 0.2 mg/kg is generally adequate. However, dose ranges of from 0.0125 to 5 mg/kg given from 1 to 10 times separated by intervals of from 1 day to 1 month are also efficacious (see Blair et al. Supra Campbell et al. Supra and Jackson et al. Supra page 131 et. seq.). Typical oral and parenteral formulations for ivermectin and other avermectin compounds are disclosed in the above noted U.S. patents. However a typical formulation suitable for administration to dogs is described below. The synergistic effects of the instant invention in treating adult canine heartworm are observed in the following example which is not to be construed as limitative of the invention.

EXAMPLE 1

Fifteen microfilaria positive mixed breed random source dogs were purchased from three commerical canine suppliers. They were held in a screened building several months before treatment with thiacetarsamide sodium and ivermectin to treat the dogs for their adult worm infections. In line with the recommendations of the counsel of the American Veterinary Medical Association and the Executive Committee of the American Heartworm Society, each dog received 0.1 ml fluid per pound of thiacetarsamide sodium solution (10 mg per ml) for a dose of 1 mg/lb, intravenously twice daily for two consecutive days. For this study, treatments were given at 8:30 AM and 3:30 PM, 43 and 42 days before the ivermectin treatment. Each dog also received 0.75 mg of dexamethasone prior to the morning thiacetarsamide treatment.

Six weeks after the thiacetarsamide treatment the dogs were subdivided by restricted randomization based on level of microfilaremia into five (5) groups. Controls (3 dogs) received single oral doses of propylene glycol at a dosage of 0.1 mg/kg of body weight. The remaining dogs received single oral doses of ivermectin in a comparable volume of propylene glycol as follows: 0.2 mg/kg (3 dogs): 0.05 ml/kg (3 dogs): 0.0125 ml/kg (3 dogs): and 0.00313 ml/kg (2 dogs). The dogs were caged individually for at least two weeks following invermectin treatment.

All dogs were euthanized 23 days post-ivermectin treatment. The heart and lungs of each dog were removed and examined for live heartworms and/or evidence of dead worms. The results of the test are seen in the following table.

Effect of Ivermectin and Thiacetarsemide on Adult Canine Heartworms:

| Group | | Live Adult Worms | | |
|---|---|---|---|---|
| Dose-Ivermectin | Dog No. | Male | Female | Total |
| I | | | | |
| 0.2 mg/kg | 3004M | 0 | 0 | 0 |
| | 2837M | 0 | 0 | 0 |
| | 2838M | 0 | 0 | 0 |
| II | | | | |
| 0.05 mg/kg | 13297M | 0 | 0 | 0 |
| | 3067M | 0 | 0 | 0 |
| | 2831M | 0 | 0 | 0 |
| III | | | | |
| 0.0125 mg/kg | 5291M | 0 | 0 | 0 |
| | 2836M | 0 | 0 | 0 |
| | 2832M | 0 | 0 | 0 |
| IV | | | | |
| 0.00313 mg/kg | 3066M | 0 | 1 | 1 |
| | 2830F | 0 | 1 | 1 |
| V - Control | | | | |
| 0 mg/kg | 2825M | 0 | 0 | 0 |
| | 2829F | 0 | 1 | 1 |
| | 2833M | 0 | 1 | 1 |

All groups were treated 6 weeks prior to ivermectin treatment with 1 mg/lb. (2.2 mg/kg) of thiacetarsamide twice a day for 2 consecutive days.

As is readily observed, the treatment with thiacetarsamide alone (Group V) was not completely efficacious since two dogs had one each of live adult heart worms. Only one dog out of the three was free of live adult worms. The groups treated with ivermectin 6 weeks subsequent to the thiacetarsamide treatment were (accept for the lowest dose tested) completely free of adult worms.

Thus the combination of an incompletely active adult filaraside with another drug which has no adulticidal activity is seen to be completely efficacious against adult canine heartworm at doses of from about 0.0125 mg/kg and higher.

EXAMPLE 2

An Oral Formulation of Ivermectin for Use Against Adult Canine Heartworms

A 2 mg/ml solution of ivermectin is prepared by dissolving 20 mg of ivermectin in 10 ml of propylene glycol. The compound is readily soluble in propylene glycol. This solution is used as a stock solution and is diluted as necessary with additional propylene glycol to prepare the concentrations used in Example 1.

What is claimed is:

1. A synergistic method for the elimination of adult canine heartworms (Dirofilaria imitis) from dogs so infected which comprises the intravenous administration to said dogs of about 1 mg per lb. (2.2 mg/kg) of thiacetarsamide followed by the administration either orally or parenterally of from 0.0125 to 5 mg/kg of ivermectin administered at from 3 to 6 weeks after the thiacetarsamide administration in a single dose or multiple doses given at from 1 day to 1 month intervals.

2. The method of claim 1 wherein the ivermectin is given in a single dose at from 3 to 6 weeks after the thiacetarsamide administration.

3. The method of claim 2 wherein the ivermectin is given at about 0.05 to 0.3 mg/kg.

4. The method of claim 3 wherein the ivermectin is given at about 0.2 mg/kg.

* * * * *